United States Patent
Awad et al.

(10) Patent No.: US 10,398,744 B1
(45) Date of Patent: Sep. 3, 2019

(54) SYNTHESIS OF MUSTARD SEED NANOPARTICLES

(71) Applicant: KING SAUD UNIVERSITY, Riyadh (SA)

(72) Inventors: Manal Ahmed Gasmelseed Awad, Riyadh (SA); Promy Virk, Riyadh (SA); Rabia Qindeel, Riyadh (SA); Khalid Mustafa Osman Ortashi, Riyadh (SA); Mai Abdelrahman Elobeid, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/270,914

(22) Filed: Feb. 8, 2019

(51) Int. Cl.
    *A61K 36/00* (2006.01)
    *A61K 36/31* (2006.01)
    *A61K 9/51* (2006.01)

(52) U.S. Cl.
    CPC ............ *A61K 36/31* (2013.01); *A61K 9/5192* (2013.01); *A61K 2236/15* (2013.01); *A61K 2236/31* (2013.01); *A61K 2236/53* (2013.01)

(58) Field of Classification Search
    None
    See application file for complete search history.

(56) References Cited

U.S. PATENT DOCUMENTS 9,539,217 B2    1/2017    Sosin et al.

FOREIGN PATENT DOCUMENTS

CN    103653174 A  *  3/2014
CN    104383008 A     3/2015

OTHER PUBLICATIONS

Priyanka Bassan et al., "Antioxidant and in vitro Anti-cancer Activities of *Brassia juncea* (L.) Czern, seeds and sprouts," Int, J. of Pharma Sci. (3)5, pp. 343-349 (2013).

Reka Szollosi, "Chapter 78—Indian; Mustard (*Brassica juncea* L.) Seeds in Health" Nuts and Seeds in Health and Disease Prevention, pp. 671-676 (2011).

M. Khatami et al., "Biogenic Synthesis of Silver Nanoparticles Using Mustard and Its Characterization," Int. J Nanosci. Nanotechnol., (11)4 pp. 281-288 (2015).

Ram Prasad, "Synthesis of Silver Nanoparticles in Photosynthetic Plants," J. of Nanoparticles (2014).

Manisha D.R. et al., "Biofabrication of antibacterial silver nanoparticles from black mustard seed powder and their characterization," Int. J. of Nanomaterials and Biostructures (4)3 pp. 58-62 (2014).

* cited by examiner

*Primary Examiner* — Qiuwen Mi
(74) *Attorney, Agent, or Firm* — Richard C. Litman

(57) ABSTRACT

The mustard seed nanoparticles may be synthesized by washing mustard seeds, drying and crushing the washed mustard seeds, extracting the crushed mustard seeds to produce a mustard seed extract, spraying the mustard seed extract into boiling water, sonicating the mustard seed extract and boiling water mixture, and centrifuging the mustard seed extract and boiling water mixture to obtain mustard seed nanoparticles. The mustard seed nanoparticles may be used in a pharmaceutical composition.

8 Claims, 4 Drawing Sheets

SYNTHESIS OF MUSTARD SEED NANOPARTICLES

BACKGROUND

1. Field

The disclosure of the present patent application relates to green nanotechnology, and particularly to the synthesis and use of mustard seed nanoparticles.

2. Description of the Related Art

In materials science, nanomaterials have demonstrated unique size and morphology based characteristics. Nanotechnology is an emerging field demonstrating significant potential for the development of new medicines and drug delivery. Entrapment of active ingredients in polymeric nanoparticles results in improved stability, uptake, and distribution profiles. The most common methods of producing nanoparticles are chemical or mechanical, including ball milling, thermal quenching, precipitation techniques, and vapor deposition. However, these methods are often costly, and may result in toxic byproducts.

Biological approaches have also been developed, including use of plant extracts to synthesize metal nanoparticles, such as silver nanoparticles. Silver nanoparticles are of particular interest due to their antibacterial properties.

Mustard seeds have been shown to possess compounds with antibacterial, insecticidal, nematocidal, antifungal, and anticancer activities. Mustard seed extracts have been investigated for antioxidant and anticancer activities. *Brassica juncea*, also known as the Indian mustard or brown mustard, has been used to treat rheumatism, respiratory infections, the common cold, and arthritis, and to relieve water retention.

Thus, a method of synthesizing mustard seed nanoparticles are desired.

SUMMARY

A method of synthesizing mustard seed nanoparticles may include washing mustard seeds, drying and crushing the washed mustard seeds, extracting the crushed mustard seeds to produce a mustard seed extract, spraying the mustard seed extract into boiling water under ultrasonic conditions, and centrifuging the mustard seed extract and boiling water mixture to obtain mustard seed nanoparticles.

An embodiment of the present subject matter includes a pharmaceutical composition including the mustard seed nanoparticles.

An embodiment of the present subject matter is directed to a pharmaceutical composition including the mustard seed nanoparticles and a pharmaceutically acceptable carrier.

An embodiment of the present subject matter is directed to a method of making a pharmaceutical composition including mixing the mustard seed nanoparticles under sterile conditions with a pharmaceutically acceptable carrier and preservatives, buffers, or propellants to create the pharmaceutical composition; and providing the pharmaceutical composition in a form suitable for daily, weekly, or monthly administration.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
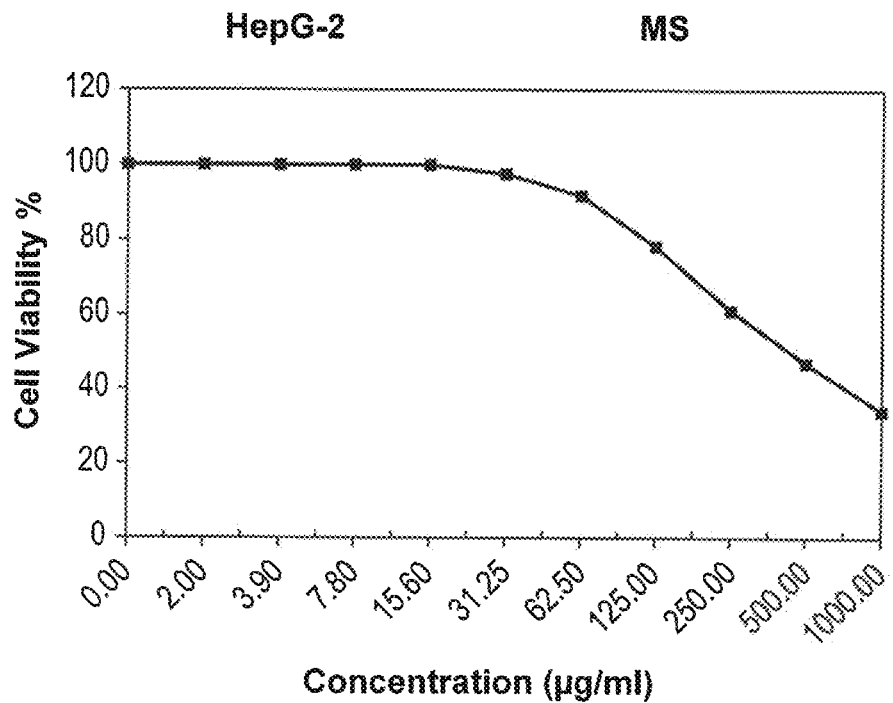
FIG. 1 depicts a graph of cytotoxicity of mustard seed powder against HepG-2 cells.

The mustard seed nanoparticles may be synthesized by washing mustard seeds, drying and crushing the washed mustard seeds, extracting the crushed mustard seeds to produce a mustard seed extract, spraying the mustard seed extract into boiling water under ultrasonic conditions to provide a mixture, and centrifuging the mustard seed extract and boiling water mixture to obtain mustard seed nanoparticles.

As used herein, the term "about," when used to modify a numerical value, means within ten percent of that numerical value.

In an embodiment, the mustard seeds may be *Brassica juncea* seeds, commonly known as brown mustard.

In an embodiment, the crushed mustard seed may be prepared by adding the crushed mustard seeds to dimethyl sulfoxide (DMSO). For example, about 400 mg of the mustard seeds may be extracted in about 30 ml of DMSO.

In an embodiment, the mustard seed extract may be sprayed into about 50 ml of boiling water, dropwise, with a flow rate of about 0.2 mL/min, over about 5 minutes, under ultrasonic conditions.

In an embodiment the sonicating of the mustard seed extract and boiling water mixture may occur for about 5 minutes, and thereafter the sonicated mixture may be stirred at about 200-800 rpm at room temperature for about 20 minutes.

In an embodiment, the mustard seed nanoparticles may be used to treat or inhibit the growth of cancerous cells. The cancerous cells may be liver cancer cells, breast cancer cells, or the like.

An embodiment of the present subject matter is directed to a pharmaceutical composition comprising the mustard seed nanoparticles and a pharmaceutically acceptable carrier.

An embodiment of the present subject matter is directed to a method of making a pharmaceutical composition including mixing the mustard seed nanoparticles with a pharmaceutically acceptable carrier. For example, the method of making a pharmaceutical composition can include mixing the mustard seed nanoparticles under sterile conditions with a pharmaceutically acceptable carrier, and optionally, preservatives, buffers, and/or propellants.

An embodiment of the present subject matter is directed to a pharmaceutical composition including the mustard seed nanoparticles. To prepare the pharmaceutical composition, the mustard seed nanoparticles, as the active ingredient, are intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by inhalation or insufflation. The nanoparticles can be mixed under sterile conditions with a pharmaceutically acceptable carrier and, if required, any needed preservatives, buffers, or propellants. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose. A therapeutically effective amount of the mustard seed nanoparticles or an amount effective to treat a disease, such as a disease associated with liver cancer or breast cancer, may be determined initially from the Examples described herein and adjusted for specific targeted diseases using routine methods.

The following examples illustrate the present teachings.

Example 1

Synthesis and Characterization of Mustard Seed Nanoparticles

Mustard seeds were washed in tap water and dried. The dried mustard seeds were then crushed using a mechanical grinder to produce a mustard seed powder which was brown in appearance. The mustard seed powder (about 400 mg) was dissolved in about 30 ml of Dimethyl sulfoxide (DMSO) under stirring to provide a first solution. The first solution was sprayed into about 50 ml boiling water, dropwise with a flow rate of about 0.2 ml/min, for about 5 min. under ultrasonic conditions, with an ultrasonic power of about 750 W and a frequency of about 20 kHz, producing a second solution. After about 5 min. of sonication, the second solution was stirred at about 200-800 rpm at room temperature for about 20 min. The second solution was then centrifuged and dried to obtain mustard seed nanoparticles.

Figure 5:
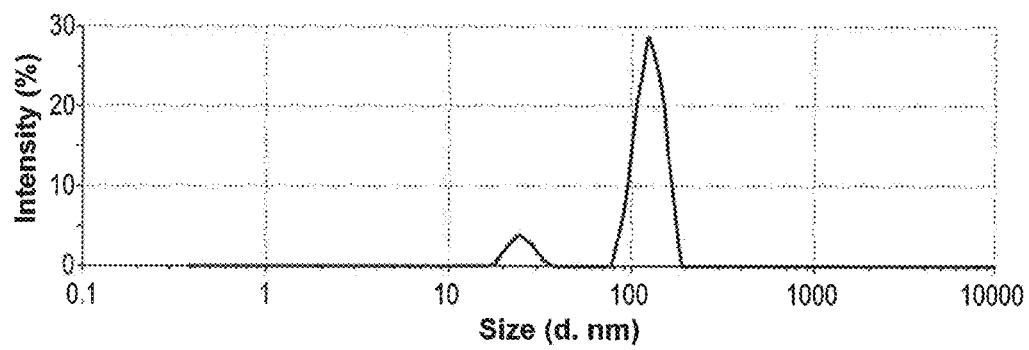
FIG. 5 depicts a zeta-sizer spectrum of the diameter of the mustard seed nanoparticles.
Figure 6A:
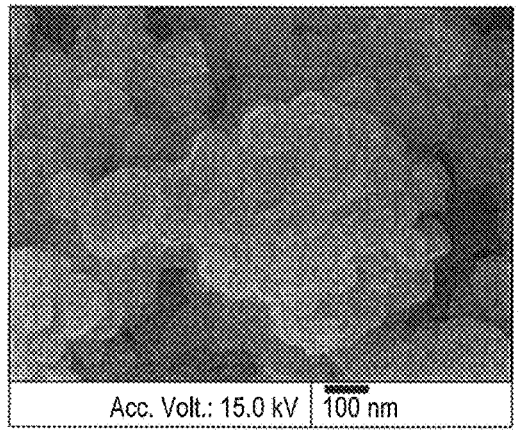
FIG. 6A depicts a scanning electron micrograph of the mustard seed nanoparticles.
Figure 6B:
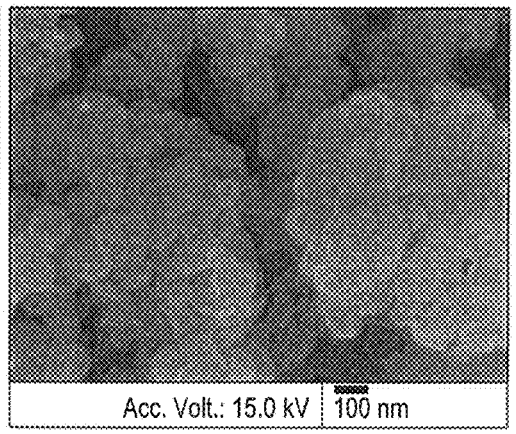
FIG. 6B depicts a scanning electron micrograph of the mustard seed nanoparticles.
Figure 6C:
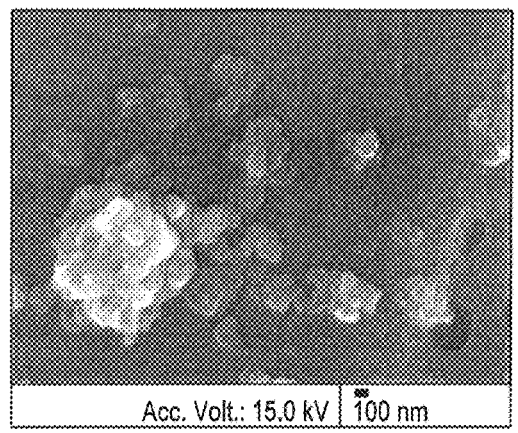
FIG. 6C depicts a scanning electron micrograph of the mustard seed nanoparticles.

The resulting mustard seed nanoparticles were characterized using scanning electron microscopy and zeta-sizer analysis. The scanning electron micrographs demonstrated that a particle size of the mustard seed nanoparticles ranging from about 10 nm to about 200 nm (see FIGS. 6A-6C). As further illustrated in FIGS. 6A-6C, the mustard seed nanoparticles are poly-dispersed spherical nanoparticles. The zeta-size analysis found an actual diameter size of the nanoparticles ranging from about 10 nm to about 100 nm. (See FIG. 5). However, as further illustrated in FIG. 5, the zeta-size analysis also found an average diameter size of 349.9 nm, which may result from a lipid layer and/or seed coat surrounding the nanoparticles.

Example 2

Experimental Conditions for Evaluating Cytotoxic Effects of Nanoparticles

MCF-7 and HepG-2 cell lines were obtained from the VACSERA Tissue Culture Unit. Dimethyl sulfoxide (DMSO), crystal violet, and trypan blue were purchased from Sigma. Fetal Bovine Serum (FBS), Dulbecco's Modified Eagle's Medium (DMEM), RPMI-1640, HEPES buffer solution, L-glutamine, gentamycin, and 0.255 Trypsin-EDTA were purchased from Lonza. The crystal violet stain (1%) was prepared by mixing 0.5% (w/v) crystal violet and 50% methanol, q.s. with $ddH_2O$, and filtering this solution through Whatmann No. 1 filter paper.

Cells were propagated in DMEM supplemented with 10% heat-inactivated FBS, 1% L-glutamine, HEPES buffer and 50 µg/ml gentamycin. All cells were maintained at 37° C. in a humidified atmosphere with 5% $CO_2$, and were sub-cultured two times a week.

For the cytotoxicity assays, cells were seeded in 96-well plate at a cell concentration of $1 \times 10^4$ cells per well in 100 µl of growth medium. Fresh medium containing different concentrations of the test sample was added 24 h after seeding. Serial two-fold dilutions of the tested compound were added to confluent cell monolayers dispensed into 96-well, flat-bottomed microtiter plates (Falcon, NJ, USA) using a multichannel pipette. The microtiter plates were incubated at 37° C. in a humidified incubator with 5% $CO_2$ for a period of 48 h. Three wells were used for each concentration of the test sample. Control cells were incubated without test sample and with or without DMSO. The low percentage of DMSO present in the wells (maximal 0.1%) was found not to affect the experiment. After incubation of the cells at 37° C., various concentrations of sample were added, and incubation was continued for 24 h and viable cell yield was determined by a colorimetric method.

In brief, after the end of the incubation period, media were aspirated and crystal violet solution (1%) was added to each well for at least 30 minutes. The stain was removed and the plates were rinsed using tap water until all excess stain was removed. Glacial acetic acid (30%) was then added to all wells and mixed thoroughly, and then the absorbance of the plates were measured after gently shaken on Microplate reader (TECAN, Inc.), using a test wavelength of 490 nm. All results were corrected for background absorbance detected in wells without added stain. Treated samples were compared with the cell control in the absence of the tested compounds. All experiments were carried out in triplicate. The cell cytotoxic effect of each tested compound was calculated. The optical density was measured with the microplate reader (SunRise, TECAN, Inc, USA) to determine the number of viable cells and the percentage of viability was calculated as $[1-(ODt/ODc)] \times 100\%$ where ODt is the mean optical density of wells treated with the tested sample and ODc is the mean optical density of untreated cells. The relation between surviving cells and drug concentration was plotted to get the survival curve of each tumor cell line after treatment with the specified compound. The 50% inhibitory concentration (IC50), the concentration required to cause toxic effects in 50% of intact cells, was estimated from graphic plots of the dose response curve for each conc. using Graphpad Prism software (San Diego, Calif. USA).

Example 3

Figure 2:
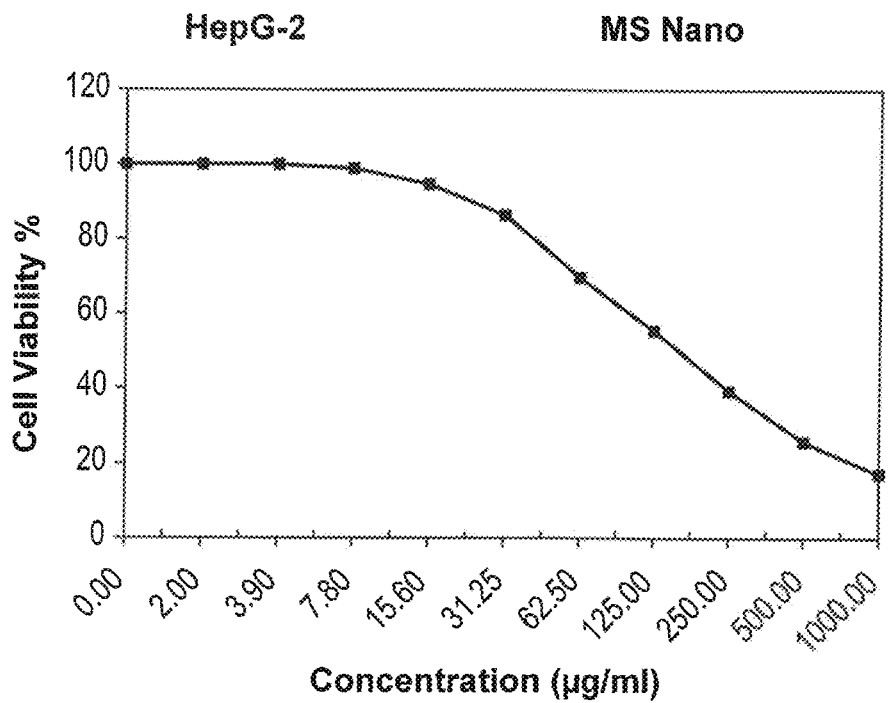
FIG. 2 depicts a graph of cytotoxicity of mustard seed nanoparticles against HepG-2 cells.

Cytotoxicity of Mustard Seed Powder and Mustard Seed Nanoparticles to HepG-2 and MCF-7 Cells The cytotoxicity of both the mustard seed powder and the mustard seed nanoparticles (prepared according to Example 1) was tested using the method of Example 2. The results of these experiments are illustrated in Tables 1 & 2 and in FIG. 1 and FIG. 2, respectively.

TABLE 1

Cytotoxicity of Mustard Seed Powder in HepG-2 Cells

| µg/ml | Viability % | | | Mean | Inhibitory % | S.D. (±) |
|---|---|---|---|---|---|---|
| 1000 | 38.91 | 32.74 | 30.52 | 34.06 | 65.94 | 4.35 |
| 500 | 49.23 | 46.56 | 45.17 | 46.99 | 53.01 | 2.06 |
| 250 | 64.37 | 60.98 | 58.25 | 61.20 | 38.80 | 3.07 |
| 125 | 81.65 | 79.82 | 73.46 | 78.31 | 21.69 | 4.30 |
| 62.5 | 92.41 | 97.63 | 85.21 | 91.75 | 8.25 | 6.24 |
| 31.25 | 98.62 | 99.87 | 94.25 | 97.58 | 2.42 | 2.95 |
| 15.6 | 100 | 100 | 99.87 | 99.96 | 0.04 | 0.08 |
| 7.8 | 100 | 100 | 100 | 100 | 0 | 0 |
| 3.9 | 100 | 100 | 100 | 100 | 0 | 0 |
| 2 | 100 | 100 | 100 | 100 | 0 | 0 |
| 0 | 100 | 100 | 100 | 100 | 0 | 0 |

TABLE 2

Cytotoxicity of Mustard Seed Nanoparticles in HepG-2 Cells

| µg/ml | Viability % | | | Mean | Inhibitory % | S.D. (±) |
|---|---|---|---|---|---|---|
| 1000 | 17.82 | 14.97 | 19.21 | 17.33 | 82.67 | 2.16 |
| 500 | 26.9 | 23.81 | 26.9 | 25.87 | 74.13 | 1.78 |
| 250 | 37.23 | 40.72 | 39.88 | 39.28 | 60.72 | 1.82 |
| 125 | 52.06 | 56.94 | 57.31 | 55.44 | 44.56 | 2.93 |
| 62.5 | 67.34 | 72.18 | 69.4 | 69.64 | 30.36 | 2.43 |
| 31.25 | 85.62 | 89.41 | 84.23 | 86.42 | 13.58 | 2.68 |
| 15.6 | 95.21 | 96.8 | 82.37 | 94.79 | 5.21 | 2.24 |
| 7.8 | 99.76 | 99.76 | 97.43 | 98.98 | 1.02 | 1.35 |
| 3.9 | 100 | 100 | 100 | 100 | 0 | 0 |
| 2 | 100 | 100 | 100 | 100 | 0 | 0 |
| 0 | 100 | 100 | 100 | 100 | 0 | 0 |

The cytotoxic effect of the mustard seed nanoparticles on cancer cell lines (MCF-7 and HepG-2) used in the present study was more profound than the effect of the mustard seed powder. At a high concentration (1000 µg/ml) the mustard seed nanoparticles had an inhibitory percentage of 82.67 on HepG-2 cell growth, while the mustard seed powder showed an inhibitory percentage of 65.94 at the same concentration (Tables 1-2 and FIGS. 1-2). For the mustard seed nanoparticles, the inhibitory effect on HepG-2 cell growth was detectable at a lower concentration of 7.8 µg/ml, while for the mustard seed powder it was observed at 31.25 µg/ml which was 4-fold more than the initial inhibitory concentration of the mustard seed nanoparticles (Tables 1-2). Similarly, the IC50 of the mustard seed extract against Hep2-G cells was 477±32.68 µg/ml, while the IC50 of the mustard seed powder was only 167-16.79 µg/ml.

TABLE 3

Cytotoxicity of Mustard Seed Powder in MCF-7 Cells

| µg/ml | Viability % | | | Mean | Inhibitory % | S.D. (±) |
|---|---|---|---|---|---|---|
| 1000 | 46.84 | 44.37 | 40.89 | 44.03 | 55.97 | 2.99 |
| 500 | 59.2 | 56.43 | 57.38 | 57.67 | 42.33 | 1.41 |
| 250 | 76.43 | 76.43 | 79.41 | 77.42 | 22.58 | 1.72 |
| 125 | 89.51 | 87.84 | 91.37 | 89.57 | 10.43 | 1.77 |
| 62.5 | 97.42 | 98.68 | 99.53 | 98.54 | 1.46 | 1.06 |
| 31.25 | 1.00 | 100 | 100 | 100 | 0 | 0 |
| 15.6 | 100 | 100 | 100 | 100 | 0 | 0 |
| 7.8 | 100 | 100 | 100 | 100 | 0 | 0 |
| 3.9 | 100 | 100 | 100 | 100 | 0 | 0 |
| 2 | 100 | 100 | 100 | 100 | 0 | 0 |
| 0 | 100 | 10.0 | 100 | 100 | 0 | 0 |

TABLE 4

Cytotoxicity of Mustard Seed Nanoparticles in MCF-7 Cells

| µg/ml | Viability % | | | Mean | Inhibitory % | S.D. (±) |
|---|---|---|---|---|---|---|
| 1000 | 25.47 | 21.89 | 27.36 | 24.91 | 75.0 | 2.78 |
| 500 | 40.89 | 36.56 | 40.89 | 39.45 | 60.55 | 2.50 |
| 250 | 53.42 | 48.17 | 56.27 | 52.62 | 47.38 | 4.11 |
| 125 | 70.84 | 65.92 | 71.43 | 69.40 | 30.60 | 3.03 |
| 62.5 | 89.51 | 87.24 | 87.24 | 88.00 | 12.00 | 1.31 |
| 31.25 | 97.26 | 95.31 | 96.86 | 96.48 | 3.52 | 1.03 |
| 15.6 | 100 | 98.64 | 99.72 | 99.45 | 0.55 | 0.72 |
| 7.8 | 100 | 100 | 100 | 100 | 0 | 0 |
| 3.9 | 100 | 100 | 100 | 100 | 0 | 0 |
| 7 | 100 | 100 | 100 | 100 | 0 | 0 |
| 0 | 100 | 100 | 100 | 100 | 0 | 0 |

Figure 3:
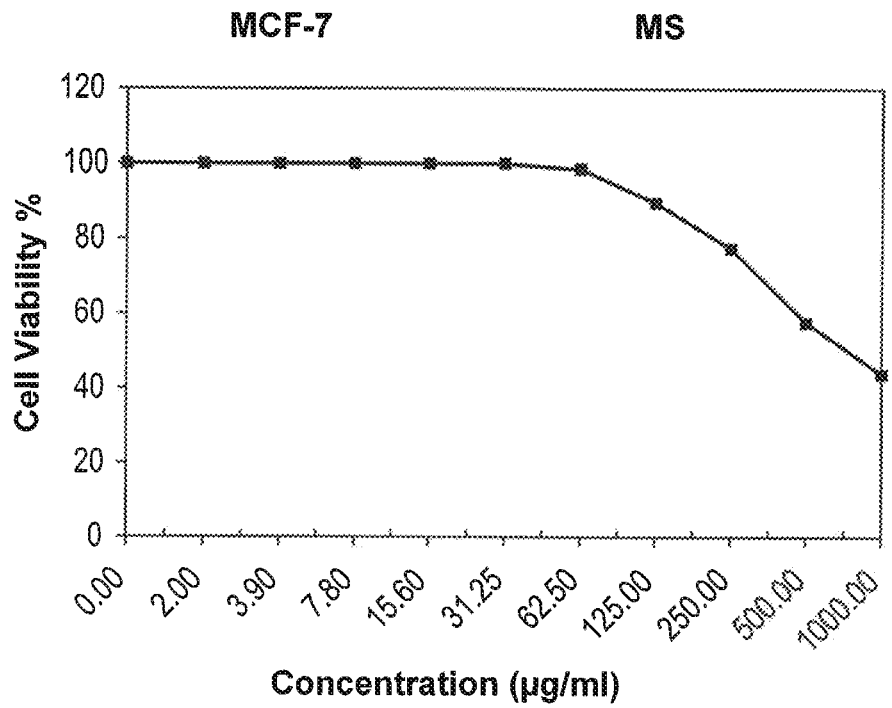
FIG. 3 depicts a graph of cytotoxicity of mustard seed powder against MCF-7 cells.
Figure 4:
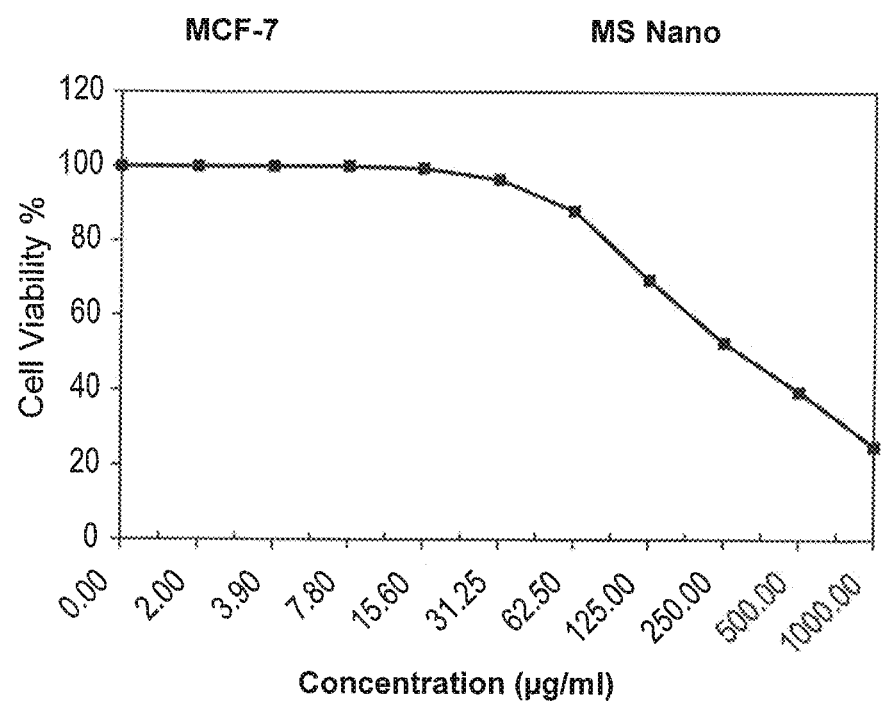
FIG. 4 depicts a graph of cytotoxicity of mustard seed nanoparticles against MCF-7 cells.

For the MCF-7 cells, the mustard seed nanoparticles produced an inhibitory percentage at the highest tested concentration (10004 g/ml) of 75.09, while the mustard seed powder at the same test concentration produced an inhibitory percentage of only 55.97 (See Tables 3-4 and FIGS. 3-4). Further, for the mustard seed nanoparticles, an inhibitory effect on the MCF-7 cells was detectable at a lower concentration of 15.6 µg/ml while for the mustard seed powder the inhibitory effect was first observed at 62.5 µg/ml (Tables 3-4). Similarly, the IC50 of the mustard seed powder against MCF-7 cells was 781.1±62.44 µg/ml, while the IC50 of the mustard seed nanoparticles against MCF-7 cells was only 299.7±60.3 µg/ml.

It is to be understood that the synthesis of mustard seed nanoparticles is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of fabricating mustard seed nanoparticles, comprising:
   (a) crushing mustard seeds to produce mustard seed powder;
   (b) extracting the mustard seed powder to produce a first solution;
   (c) spraying the first solution into boiling water under ultrasonic conditions to produce a second solution; and
   (d) centrifuging and drying the sonicated second solution to obtain mustard seed nanoparticles.

2. The method of fabricating mustard seed nanoparticles of claim 1, wherein the mustard seeds are *Brassica juncea* seeds.

3. The method of fabricating mustard seed nanoparticles of claim 1, wherein about 400 mg of the mustard seed powder is extracted in about 30 ml dimethyl sulfoxide.

4. The method of fabricating mustard seed nanoparticles of claim 1, wherein the first solution is sprayed into about 50 ml of boiling water, dropwise, with a flow rate of about 0.2 ml/min, over about 5 minutes, under ultrasonic conditions.

5. The method of fabricating mustard seed nanoparticles of claim 1, wherein the second solution is sonicated for about 5 minutes.

6. The method of fabricating mustard seed nanoparticles of claim 1, further comprising washing and drying the mustard seeds before crushing the mustard seeds to produce the mustard seed powder.

7. The method of fabricating mustard seed nanoparticles of claim 1, further comprising stirring the sonicated second solution at about 200-800 rpm at room temperature for about 20 minutes.

8. A method of fabricating mustard seed nanoparticles, comprising:
   (a) crushing mustard seeds to produce mustard seed powder;
   (b) adding the mustard seed powder to dimethyl sulfoxide to produce an extract;
   (c) spraying the extract into boiling water under ultrasonic conditions to produce a sonicated solution; and
   (d) centrifuging and drying the sonicated solution to obtain mustard seed nanoparticles,
   wherein the mustard seeds are *Brassica juncea* seeds.

\* \* \* \* \*